United States Patent [19]

John

[11] 4,153,677

[45] May 8, 1979

[54] CONTROLLED-RELEASE COMPOSITION

[75] Inventor: Philip M. John, East Greenbush, N.Y.

[73] Assignee: Sterling Drug Inc., New York, N.Y.

[21] Appl. No.: 907,036

[22] Filed: May 18, 1978

[51] Int. Cl.² .......................... A61K 9/48; A61K 9/50; A61K 9/52

[52] U.S. Cl. ........................................ 424/19; 424/35; 424/37

[58] Field of Search ..................................... 424/19–22, 424/35

[56] References Cited

U.S. PATENT DOCUMENTS

| | | | |
|---|---|---|---|
| 3,247,066 | 4/1966 | Milosovich | 424/35 X |
| 3,400,185 | 9/1968 | Kohnle et al. | 424/35 X |
| 3,488,418 | 1/1970 | Holliday et al. | 424/35 X |
| 3,492,397 | 1/1970 | Peters et al. | 424/35 X |
| 3,524,910 | 8/1970 | Holliday et al. | 424/35 X |
| 3,538,214 | 11/1970 | Polli et al. | 424/35 X |
| 3,632,739 | 1/1972 | Kornblum | 424/35 X |
| 3,835,221 | 9/1974 | Fulberth et al. | 424/35 X |
| 3,909,444 | 9/1975 | Anderson et al. | 424/35 X |
| 3,917,813 | 11/1975 | Pedersen | 424/35 X |
| 4,083,949 | 4/1978 | Benedikt | 424/35 X |

*Primary Examiner*—Shep K. Rose
*Attorney, Agent, or Firm*—Paul E. Dupont; B. Woodrow Wyatt

[57] ABSTRACT

A controlled-release pharmaceutical dosage component comprising a microencapsulated bronchodilator agent of the $\beta$-adrenergic agonist type is prepared by organic phase separation. Pharmaceutical formulations containing these components exhibit prolonged bronchodilation with minimal cardiac stimulation.

12 Claims, No Drawings

CONTROLLED-RELEASE COMPOSITION

BACKGROUND OF THE INVENTION

1. Field of the Invention

This invention pertains to a novel pharmaceutical dosage component exhibiting a controlled rate of release of a bronchodilator agent of the β-adrenergic agonist type.

2. Prior Art

The technique of microencapsulation of pharmaceutical substances is generally known [Phares and Sperandio, J. Pharm. Sci. 53, 515–518 (1964) and Luzzi, J. Pharm. Sci. 59, 1367–1376 (1970)].

Microencapsulation of a number of pharmaceuticals with ethylcellulose by organic phase separation is also known and is described in Miller and Anderson U.S. Pat. No. 3,155,590, Anderson et al. U.S. Pat. No. 3,341,416, and Powell and Anderson U.S. Pat. No. 3,576,759, issued Nov. 3, 1964, Sept. 12, 1967 and Apr. 27, 1971, respectively, and in Holliday et al. U.S. Pat. Nos. 3,488,418 and 3,524,910, issued Jan. 6 and Aug. 18, 1970, respectively.

Bronchodilator agents of the β-adrenergic agonist type constitute a well-known class of pharmaceutical compounds (AMA Drug Evaluation, 3rd Edition, Publishing Sciences Group Inc., Littleton, Mass., 1977, pgs. 631–636 and W. C. Cutting, Cutting's Handbook of Pharmacology, 5th Edition, Meridan Corp., New York, 1972, pgs. 424–435). These compounds usually affect the adrenergic receptors of both the lungs (β-2) and the heart (β-1), thus producing bronchial relaxation (bronchodilation) accompanied by cardiac stimulation (tachycardia). Published reports show that much effort has been expended in attempting to separate the β-1 and β-2 effects of β-adrenergic agents with only partial success and accordingly, research directed at divorcing the cardiac effects from the bronchial effects continues.

SUMMARY OF THE INVENTION

It has now been found that bronchodilator agents of the β-adrenergic agonist type, when microencapsulated in a suitable polymeric film, are effective in producing bronchodilation of extended duration with an unexpected attenuation of the accompanying tachycardia usually produced by such bronchodilator agents.

Accordingly, the invention sought to be patented resides in a controlled-release pharmaceutical dosage component comprising a microcapsule consisting of a film of hydrophobic polymeric material encapsulating a core comprising a bronchodilator agent of the β-adrenergic agonist type in admixture with a pharmaceutically acceptable excipient.

The invention also comprehends the above components in a pharmaceutical formulation in unit dosage form.

DETAILED DESCRIPTION INCLUSIVE OF THE PREFERRED EMBODIMENTS

The present invention can be applied to any bronchodilator of the well-known class of bronchodilators of the β-adrenergic agonist type which act primarily on the β-adrenergic receptors of the lungs (β-2) and to a lesser extent on the β-adrenergic receptors of the heart (β-1). Among the foregoing are included for example 3,4-dihydroxy-α-[(methylamino)-methyl]benzenemethanol, α-[1-(methylamino)ethyl]benzenemethanol, α-(1-aminoethyl)benzenemethanol, α-(1-aminopropyl)-3,4-dihydroxybenzenemethanol, 3,4-dihydroxy-α-[(isopropylamino)methyl]benzenemethanol, 3,5-dihydroxy-α-[(isopropylamino)methyl]benzenemethanol, 3,4-dihydroxy-α-<{[2-(3,4-methylenedioxyphenyl)-1-methylethyl]amino}methyl>benzenemethanol, α-[(tert-butylamino)-methyl]-3,4-dihydroxybenzenemethanol, α-[(tert-butylamino)methyl]-3,5-dihydroxybenzenemethanol, 3,4-dihydroxy-α-[1-isopropylamino)propyl]benzenemethanol, 4-hydroxy-3-(hydroxymethyl)-α-[(tert-butylamino)methyl]benzenemethanol, 4-hydroxy-α-[(isopropylamino)methyl]-3-(methanesulfonamido)benzenemethanol, 3,5-dihydroxy-α-<{[2-(4-hydroxyphenyl)-1-methylethyl]amino}methyl>-benzenemethanol, 3,4-dihydroxy-α-(2-piperidinylmethyl)benzenemethanol, 2-chloro-α-[(isopropylamino)methyl]benzenemethanol, 3-hydroxy-α-[(methylamino)methyl]benzenemethanol, 4-hydroxy-α-[(isopropylamino)methyl]benzenemethanol, 4-(p-chlorophenyl)-4-hydroxy-2-methylpyrrolidine, 8-hydroxy-5-[1-hydroxy-2-(isopropylamino)ethyl]quinoline, α-[(tert-butylamino)methyl]-4-hydroxy-3-(methylsulfonylmethyl)benzenemethanol and pharmaceutically acceptable acid-addition salts thereof. Preferred bronchodilator agents are those having Formula I or II

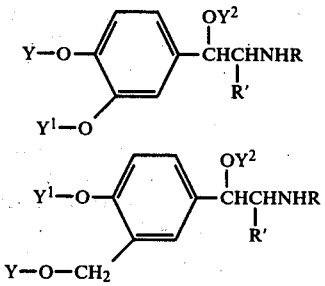

wherein in each of the above formulas:

R is hydrogen, alkyl having 1–4 carbon atoms, or cycloalkyl having 3–6 carbon atoms;

R' is hydrogen or alkyl having 1–3 carbon atoms;

Y is an acyl member which is alkanoyl having 1–22 carbon atoms, alkenoyl having one or two double bonds and having 4–22 carbon atoms, cycloalkyl—$C_nH_{2n}$—CO— having a total of 4–10 carbon atoms of which 3–7 are ring carbon atoms in cycloalkyl and wherein n is zero, one or two, 1- or 2-adamantanecarbonyl, phenoxyacetyl, naphthalenecarbonyl, pyridinecarbonyl, or Z—$C_nH_{2n}$—CO— wherein n is zero, one or two and Z is phenyl or phenyl substituted by 1–3 members of the group consisting of alkyl having 1–4 carbon atoms, alkoxy having 1–4 carbon atoms, halo, trifluoromethyl, dialkylamino having 2–8 carbon atoms, and alkanoylamino having 1–6 carbon atoms; and $Y^1$ and $Y^2$ are the same or different and are hydrogen or one of the acyl members defined by Y;

or an acid-addition salt thereof. These compounds are described in Minatoya et al. U.S. Pat. No. 3,904,671, issued Sept. 9, 1975. Among the foregoing, a particularly preferred species is 3,4-bis-(p-toluyloxy)-α-[(tert-butylamino)methyl]-benzenemethanol which has the U.S.A.N. generic name bitolterol [B. F. Tullar, H. Minatoya and R. R. Lorenz, J. Med. Chem. 19, 834 (1976)].

The bronchodilator agents can be microencapsulated by any of the known methods for microencapsulating medicaments such as spraying, coating or rolling as described by Luzzi [J. Pharm. Sci. 59, 1367–1376

(1970)] and Sliwka [Angew. Chem. internat. edit. 14, 539–550 (1975)]. For example, the bronchodilator agent either alone or in admixture with conventional excipients is spray-coated with a film of hydrophobic polymeric material as described by Caldwell and Rosen, J. Pharm. Sci. 53, 1387–1391 (1964). Alternatively and preferably, the microcapsules of this invention are prepared by coating the bronchodilator agent with a hydrophobic polymeric material employing the technique known as organic phase separation essentially as described in Anderson et al. U.S. Pat. No. 3,341,416 for the microencapsulation of aspirin particles. In this technique, cores containing the bronchodilator agent are suspended in a solution of a film-forming hydrophobic polymer in an appropriate solvent at elevated temperature. Upon cooling the polymer separates from solution and deposits as a film on the cores.

Among the hydrophobic polymers which can be employed as capsule wall materials, are included natural, halogenated and synthetic rubbers, cellulose derivatives such as ethylcellulose, cellulose nitrate, benzylcellulose, cellulose acetate and cellulose butyrate; styrene-type polymers such as polystyrene and polystyrene-maleic acid; polyalkylenes such as polyethylene, polypropylene and polybutylene; polyvinyl derivatives such as polyvinyl acetate, polyvinyl chloride and polyvinyl alcohol; and polyacrylic derivatives such as polyacrylic acid, polyacrylonitrile, polymethacrylate and polybutylacrylate.

Examples of solvents which can be used include ethyl methyl ketone, isobutyl methyl ketone, acetone tetrahydrofuran, 1,4-dioxane, ethyl acetate, butyl acetate, cyclohexanone, cyclohexane, ethylene dichloride, toluene, chloroform, carbon tetrachloride and the like.

A particular combination of core material, hydrophobic polymeric microcapsule wall material, and solvent must be chosen so that (a) the hydrophobic polymeric material is insoluble in the solvent at room temperature but has increasing solubility as the temperature is raised so that the polymer which is in solution at elevated temperature separates from the solution and deposits on the core material as the temperature is lowered, and (b) the core material remains unchanged and insoluble in the solvent throughout the temperature range employed.

The cores to be microencapsulated can be prepared according to any of the methods known in the art. Thus, the bronchodilator agent can be comminuted to an appropriate particle size and microencapsulated directly. Alternatively, the bronchodilator can be coated on particles of a suitable excipient material such as non-pareil seeds of sucrose by spraying the latter with a solution of the bronchodilator agent. The coated seeds are then microencapsulated. It is preferred, however, to prepare cores by mixing the bronchodilator agent and conventional pharmaceutical excipients, which function as diluents, binders and lubricants, with water to form a damp mass which is then extruded and converted to spherules suitable for microencapsulation as described by Conine and Hadley, Drug Cosmet. Ind. 106, 38 (1970).

Various diluents which can be employed include lactose, sucrose, mannitol sorbitol dextrins, microcrystalline cellulose, calcium sulfate, dibasic calcium phosphate, fumed silicon dioxide, talc and the like. Binders include starch, methylcellulose, gelatin, acacia, polyvinylpyrrolidone, polyvinyl alcohol, hydroxypropylmethylcellulose, pre-gelatinized starches and the like. Additional inert ingredients such as lubricants, for example mineral oil, or silicones such as dimethylpolysiloxane, can be added to the core formulation if desired.

Thus, in a preferred embodiment, about 3–80 percent by weight, preferably about 5–15 percent by weight, of a bronchodilator agent preferably having Formula I or II above, 3,4-bis-(p-toluyloxy)-α-[(t-butylamino)methyl]benzenemethanol methanesulfonate being especially preferred, about 5–25 percent by weight, preferably 10–20 percent by weight, of microcrystalline cellulose, about 25–75 percent by weight, preferably about 45–60 percent by weight of lactose and about 10–25 percent by weight, preferably about 15–20 percent by weight of starch are sieved to a suitable particle size, preferably no greater than about 30-mesh, and then blended thoroughly. The resulting blend is then granulated with about 2–5 percent by weight, preferably about 3 percent by weight of starch as a 10–25 percent by weight, preferably about 15 percent by weight aqueous paste and sufficient additional water to provide a thoroughly dampened mass. The amount of additional water required is about 15–30 percent, ordinarily about 20–25 percent by weight based on the total weight of the other ingredients in the formulation. The damp granulate is extruded through a screen to give cylindrical strands about 0.8–1.0 mm. in diameter. The extrudate is then spheronized, i.e. converted into spherules by rolling the cylinderical segments in a spheronizing apparatus (Model Q-400, sold by Elanco Products Co., Indianapolis, Ind., under the trademark Marumerizer ®) operating at about 450–550 rpm to afford damp spheronized cores which are then dried at about 25°–50° C. until the moisture content is no greater than about 2 percent as determined by a moisture balance. The dried cores are then classified to remove any particles smaller than about 40-mesh (420 microns) or larger than about 16-mesh (1190 microns). Yields of about 90–95 percent are obtained.

While starch paste is advantageously used as a binder in the above procedure, it will be appreciated that a binder is not necessary in those formulations wherein the mixture of bronchodilator and diluent alone is sufficiently cohesive. For example, the use of sucrose as a diluent obviates the need for a binder because the combination of sucrose and water forms a syrup which functions as a binder in the formulation and provides a cohesive, extrudable mass.

It is important that in the above-described preferred embodiment, the core formulation contain at least about 10 percent by weight of microcrystalline cellulose which is believed to function essentially as a conditioner promoting conversion of the extruded cylindrical rods to a substantially spherical conformation. While it is not necessary, it is advantageous that the cores be spherical since the shape is easily handled and classified and is substantially uniformly coated in the microencapsulation process.

Microencapsulation of the above-described cores by phase separation is carried out as follows: about 0.2 to 1 percent by weight, preferably about 0.4 to 0.8 percent by weight of ethylcellulose and about 0.2–2 percent by weight, preferably about 1.2–1.7 percent by weight of polyethylene is dissolved in about 75–85 percent by weight of cyclohexane. The prepared cores, about 10–25 percent by weight, preferably 12–23 percent by weight are introduced and suspended by rapid agitation. The temperature is raised to the reflux temperature of the solvent and maintained for about 5 minutes. The mixture is then cooled with continued agitation to about 40° C.; the solvent is decanted and the remaining microcapsules are washed with fresh cyclohexane and dried.

Polyethylene is used in the above-described procedure as a phase-separation inducing agent. Its presence depresses the solubility of ethylcellulose and causes it to separate from solution at slightly temperature where it has better flow properties and lower viscosity. While the use of polyethylene is advantageous, it is not essential to the operability of the microencapsulation process.

The resulting microcapsules are generally spherical with a mean volume-surface diameter of about 700 to 900 microns and have a glossy surface free from gross irregularities. The ethylcellulose constitutes about 1 to 5 percent by weight of the microcapsule and ranges in thickness from about 5 to 11 microns.

The ethylcellulose content of the microcapsules depends on the ratio of core material to ethylcellulose employed in the microencapsulation process. For example, a ratio of core material to ethylcellulose of 30:1 afforded microcapsules having a film content of 3.2 percent by weight whereas reducing the ratio to 25:1 produced microcapsules with a film content of 4.0 percent by weight.

It will, of course, be appreciated that the rate at which the bronchodilator is released from the microcapsule is directly related to ethylcellulose film content. Thus, the dissolution half-life or $t_{50\%}$ (time required to release 50% of the drug content in 0.1 N hydrochloric acid as determined by the standard U.S.P. XIX Rotating Basket Dissolution Assay) has been found to range from about 40 minutes for microcapsules having an ethylcellulose content of 2.6 percent by weight to about 175 minutes for microcapsules having a 5.0 percent by weight ethylcellulose film.

It should be noted that the release rate of bronchodilator is also proportional to the thickness of the ethylcellulose film. For a given film content film thickness is inversely proportional to the surface area of the core material. Surface area can be controlled either by varying the particle size of the core material, or alternatively, by varying the concentration of core material in the microencapsulation system. For example, two samples of spheronized cores of the same average particle size were microencapsulated as above-described using the same ratios of core material to film material (30:1). In one preparation, however, the core-to-solvent ratio was 0.15:1 while in the other, the ratio was 0.30:1. There was virtually no difference in the ethylcellulose content of the two products (3.2 and 3.1 percent by weight, respectively), however, the mean volume-surface diameters as determined by microscopic particle size analysis were 861 and 1020 microns, respectively with corresponding calculated film thicknesses of 5.6 and 6.4 microns, respectively, and dissolution half-lives ($t_{50\%}$) of 65 and 75 minutes, respectively. The greater mean volume-surface diameter of the microcapsules produced in the more concentrated system was presumably due to a greater degree of agglomeration in the latter with a resulting decrease in total surface area thus leading to deposition of a thicker film on the more concentrated core material.

For use as bronchodilator agents, the microcapsules can be formulated with pharmaceutically acceptable excipients conventionally employed for oral or parenteral administration of such agents. Ordinarily they are combined with conventional solid or liquid diluents and carriers in capsules, syrups, emulsions, suspensions or the like. It will, of course, be appreciated that the diluents and carriers must be compatible with the integrity of the ethylcellulose microcapsule wall. The formulations may contain, for example, lactose, starch, magnesium stearate, talc, gelatin, calcium carbonate, gums and the like. It is ordinarily preferred to administer these formulations orally as capsules. The individual unit dosage can be varied as desired. For general use, it is preferred to incorporate in a capsule a sufficient quantity of microcapsules to provide about 1–25 mg., preferably about 8–16 mg. of the bronchodilator agent.

The invention is further illustrated by the following examples without, however, being limited thereto.

EXAMPLE 1

Preparation of Active Cores

A. 150 Grams (5 percent by weight) of 3,4-bis-(p-toluyloxy)-α-[(tert-butylamino)methyl]benzenemethanol methanesulfonate (bitolterol), 1710 g. (57 percent by weight) of USP lactose, 570 g. (19 percent by weight) of USP microcrystalline cellulose (sold under the trade name Avicel PH 101 by the American Division of FMC Corp., Newark, Del.) and 480 g. (16 percent by weight) of USP starch were passed through a 30-mesh sieve and then blended thoroughly. The resulting blend was granulated with 90 g. (3 percent by weight) of USP starch as a 15 percent (w/w) aqueous paste and 700 ml. of water to produce a thoroughly dampened mass. This material was extruded through a 1.0 mm. screen and the extrudate was spheronized in a Marumerizer ® operating at 500 ±50 rpm. The damp spheronized cores were dried at 50° C. and then sieved to remove particles larger than 10-mesh. Of the remaining material, 89.5 percent had particles sizes >40-mesh, <16-mesh.

Preparation of Microcapsules

B. To a hot, stirred solution containing 9.5 g. of USP ethylcellulose (50–100 cps.) and 28.6 g. polyethylene (sold under the trade name Epolene Wax C-10 by Eastman Chemical Products, Inc., Kingsport, Tenn.) in 2000 ml. of cyclohexane was added 332 g. of the spheronized cores of part A above. The mixture was heated to reflux temperature (76° C.) and then allowed to cool with stirring to 30° C. After the supernatant was decanted the residue was washed with three 500-ml. portions of cold cyclohexane, collected by filtration and air dried to give 340 g. of microcapsules.

Analysis for the content of 3,4-bis-(p-toluyloxy)-α-[(tert-butylamino)methyl]benzenemethanol was carried out spectrophotometrically. A sample of microcapsules was crushed, weighed and the drug extracted therefrom with 0.1 N hydrochloric acid. Drug concentration was then determined in benzoates sample of the extract by measuring the extinction coefficient of the ultraviolet absorption band at 247 nm. and found to be 4.8 percent by weight.

Ethylcellulose present in the microcapsule was determined by a residue weight method. Approximately 5 g. of microcapsules were finely powdered, weighed and the ethylcellulose extracted therefrom by shaking 0.5 hr. with 100 ml. of chloroform. The extract was filtered and a 50-ml. aliquot of the filtrate was evaporated to dryness and constant weight in an oven at 105° C. Another 3-ml. aliquot of the filtrate was assayed for 3,4-bis-(p-toluyloxy)-α-[(tert-butylamino)methyl]-benzenemethanol to correct for extracted drug present in the ethylcellulose residue. Ethylcellulose content of the microcapsules was found to be 2.6 percent by weight.

The rate of drug release from the microcapsules was determined using a modification of the USP XIX Rotating Basket Method described in "The United States Pharmacopeia", 19th rev. Mack Publishing Co., Easton, PA 1975, pg. 651. A quantity of cores containing 15 mg. of 3,4-bis-(p-toluyloxy)-α-[(tert-butylamino)methyl]-benzenemethanol methanesulfonate was placed in the basket of the apparatus which was immersed in 250 ml. of 0.1 N hydrochloric acid at 37° C. and rotated at a rate of 100 rpm. Five-ml. aliquots were withdrawn every 15 minutes during the first hour, every 30 minutes during the second hour, and every hour thereafter. The volume of extracting medium was kept constant by addition of 5 ml. of 0.1 N hydrochloric acid following removal of each aliquot. The concentration of the drug in each aliquot was determined spectrophotometrically as described above with the following results:

| Time (min.) | Percent Drug Released |
|---|---|
| 15 | 27.8 |
| 30 | 45.8 |
| 45 | 53.6 |
| 60 | 60.7 |
| 120 | 72.9 |
| 180 | 81.5 |

Thus, the $t_{50\%}$ (time required to release 50 percent of the drug content in 0.1 N hydrochloric acid) is about 40 minutes.

EXAMPLE 2

Following a procedure similar to that described in Example 1B, but employing 280 g. of the spheronized cores of Example 1A, there was obtained 282.5 g. of microcapsules containing 4.7 percent by weight of 3,4-bis-(p-toluyloxy)-α-[(tert-butylamino)methyl]benzenemethanol methanesulfonate and 3.3 percent by weight of ethylcellulose and having a $t_{50\%}$ of about 90 minutes.

EXAMPLE 3

Preparation of Active Cores

A. 776.2 g. (12.08 percent by weight) of 3,4-bis p-toluyloxy -[(tert-butylamino)methyl]benzenemethanol methanesulfonate, 3237.6 g. (50.38 percent by weight) USP lactose, 1200.0 g. (18.67 percent by weight) of USP microcrystalline cellulose and 1020.0 g. (15.87 percent by weight) of USP starch were passed through a 30-mesh sieve and then blended thoroughly. The resulting blend was granulated with 192.8 g. (3.00 percent by weight) of USP starch as a 15 percent (w/w) aqueous paste and 1500 ml. of water to produce a thoroughly dampened mass. This material was extruded through a 1.0 mm. screen and the extrudate was spheronized in a Marumerizer ® operating at 500±50 rpm. The damp spheronized cores were dried at 40° C. and sieved to collect the spheronized cores between 16- and 40-mesh.

Preparation of Microcapsules

B. Following a procedure similar to that described in Example 1B but employing 150 g. of the spheronized cores of part A above, 5 g. of ethylcellulose, 20 g. of polyethylene and 100 ml. of cyclohexane afforded microcapsules containing 11.8 percent by weight of 3,4-bis-(p-toluyloxy)-α-[tert-butylamino)-methyl]benzenemethanol methanesulfonte and 3.2 percent by weight of ethylcellulose and having $t_{50\%}$ of 65 minutes.

C. Following a procedure similar to that described in Example 1B but employing 250 g. of the spheronized cores of part A above, 10 g. of ethylcellulose, 20 g. of polyethylene and 1000 ml. of cyclohexane afforded microcapsules containing 11.9 percent by weight of 3,4-bis-(p-toluyloxy)-α-[(tert-butylamino)methyl]benzenemethanol methanesulfonate and 4.0 percent by weight of ethylcellulose and having $t_{50\%}$ of 101 minutes.

EXAMPLE 4

Preparation of Active Cores

A. Following a procedure similar to that described in Example 3A but employing 1450 g. (12.08 percent by weight) of 3,4-bis-(p-toluyloxy)-α-[(t-butylamino)methyl]benzenemethanol methanesulfonate, 5750 g. (47.92 percent by weight) of USP lactose, 2400 g. (20.00 percent by weight) of USP microcrystalline cellulose, 2040 g. (17.00 percent by weight) of USP starch and 360 g. (3.00 percent by weight) of USP starch as a 15% (w/w) aqueous paste and 3000 ml. of water, there was obtained 10,000 g. of spheronized cores.

Preparation of Microcapsules

B. Following a procedure similar to that described in Example 1B but employing 2100 g. of the spheronized cores of part A above, 70 g. of ethylcellulose, 140 g. of polyethylene and 7000 ml. of cyclohexane afforded microcapsules containing 12.0 percent by weight of 3,4-bis-(p-toluyloxy)-α-[(t-butylamino)-methyl]benzenemethanol methanesulfonate and 3.2 percent by weight of ethylcellulose and having $t_{50\%}$ of 75 minutes.

C. Following a procedure similar to that described in Example 1B but employing 2000 g. of the spheronized cores of part A above, 80 g. of ethylcellulose, 160 g. of polyethylene and 8000 ml. of cyclohexane afforded microcapsules containing 12.0 percent by weight of 3,4-bis-(p-toluyloxy)-α-[(t-butylamino)methyl]benzenemethanol methanesulfonate and 3.6 percent by weight of ethylcellulose and having $t_{50\%}$ of 85 minutes.

D. Following a procedure similar to that described in Example 1B employing 1,600 g. of the spheronized cores of part A above, 80 g. of ethylcellulose, 160 g. polyethylene and 8000 ml. cyclohexane afforded microcapsules containing 11.8 percent by weight of 3,4-bis-(p-toluyloxy)-α-[(t-butylamino)-methyl]benzenemethanol methanesulfonate and 4.2 percent by weight of ethylcellulose and having $t_{50\%}$ of 115 minutes.

E. Following a procedure similar to that described in Example 1B but employing 2000 g. of the spheronized cores of part A above, 100 g. of ethylcellulose, 200 g. of polyethylene and 10,000 ml. of cyclohexane afforded microcapsules containing 11.8 percent by weight of 3,4-bis-(p-toluyloxy)-α-[(t-butylamino)methyl]benzenemethanol methanesulfonate and 4.6 percent by weight of ethylcellulose and having $t_{50\%}$ of 140 minutes. Another similar run afforded microcapsules containing 11.7 percent by weight of 3,4-bis-(p-toluyloxy)-α-[(t-butylamino)-methyl]benzenemethanol methanesulfonate and 5.0 percent by weight of ethylcellulose and having $t_{50\%}$ of 175 minutes.

EXAMPLE 5

150 Grams (5 percent by weight) of α-(1-aminoethyl)-benzenemethanol hydrochloride (phenylpropanolamine), 150 g. (5 percent by weight) of USP methylcellulose (15 cps), 900 g. (30 percent by weight) of USP microcrystalline cellulose and 1800 g. (60 percent by weight) of USP lactose were passed through a 30-mesh sieve and then blended thoroughly. The resulting blend was granulated with 780 ml. of water to produce a thoroughly dampened mass. This material was extruded through a 0.8 mm. screen and the extrudate was spheronized in a Marumerizer ® operating at 500±50 rpm. The damp, spheronized cores were dried at 40° C. and sieved to collect the cores between 16- and 40-mesh. By following the procedure of Example 1B, it is contemplated that these spheronized cores can be microencapsulated to produce controlled-release microcapsules containing α-(1-aminoethyl)benzenemethanol hydrochloride.

By following procedures similar to those described in Examples 1-5, but substituting the below-listed bronchodilator agents for 3,4-bis-(p-toluyloxy)-α-[(tert-butylamino)methyl]benzenemethanol methanesulfonate or α-(1-aminoethyl)benzenemethanol hydrochloride, it is contemplated that microcapsules containing 3,4-dihydroxy-α-[(isopropylamino)methyl]benzenemethanol hydrochloride; 3,4-dihydroxy-α-[(1-isopropylamino)propyl]benzenemethanol hydrochloride; 3-hydroxy-α-[(methylamino)methyl]benzenemethanol hydrochloride; 3-acetoxy-4-(p-anisoyloxy)-α-[(tert-butylamino)methyl]benzenemethanol methanesulfonate; α-[(tert-butylamino)methyl]-3,4-dihydroxy-benzenemethanol methanesulfonate; 4-hydroxy-3-hydroxymethyl-α-[(tert-butylamino)methyl]benzenemethanol sulfate or 3-pivalyloxymethyl-4-pivalyloxy-α-[(tert-butylamino)methyl]benzenemethanol methanesulfonate can be prepared.

The microencapsulated spheronized cores of the present invention are effective in producing bronchodilator activity with a minimal increase in heart rate as determined in the following tests.

Bronchodilator Activity

The bronchodilator activity of selected microencapsulated formulations of 3,4-bis-(p-toluyloxy)-α-[(t-butylamino)methyl]benzenemethanol methanesulfonate was compared to the drug as plain powder in the intact, anesthetized (pentobarbital sodium, 30 mg./kg. i.v.) open-chest dog maintained under artificial respiration using a constant volume respirator attached to a tracheal cannula. The chest cavity was opened by sternotomy and kept retracted. The opening was covered loosely with a moist gauze. A specially designed, non-rebreathing leucite valve was attached to the cannula regulating the in- and out-flows of air. Bronchoconstriction was induced by intravenous injections of histamine diphosphate (20-50 mcg./kg.). The changes in airway pressure were measured by a pressure transducer and recorded on a polygraph. The degree of bronchoconstriction was determined by measuring with a planimeter the area of the airway pressure recordings above the baseline for a 5-minute period after the histamine injection. A dose of histamine was chosen which would double the airway pressure. An initial dose of 20 mcg/kg. was given. If the airway pressure were not approximately doubled by this dose of histamine, a higher dose (30-50 mcg./kg.) was administered 30 minutes later. The response to this second dose was then used as the control, against which the bronchodilator effects of the microencapsulated products and the plain powder were measured. Bronchodilation was expressed as the percent inhibition of the control histamine-induced bronchoconstriction.

3,4-Bis-(p-toluyloxy)-α-[(t-butylamino(methyl]benzenemethanol methanesulfonate powder or formulations equivalent to 240 mcg./kg. as the base were administered directly into the duodenal lumen through a small stab opening and washed in with 2 ml. of water. The opening was then closed by suturing. The duodenum had been prepared accessible through a small midline incision in the abdomen. The first post-medication histamine injection was given at 10 minutes with subsequent injections at 30 minutes, 1 hour and hourly thereafter for 6 hours.

Intravenous injections of saline (1 ml.) were given to three dogs to assay the stability of the histamine response in this test system. Under the conditions of these experiments it was found that the degree of histamine-induced bronchoconstriction remained constant throughout the test.

Heart Rate Effect

In the heart rate study a group of six trained dogs of both sexes weighing 10–14 kg. were used repeatedly, but no more often than once a week. Food was withheld from these dogs 17-18 hours prior to the test. During the experimental sessions, the dogs were placed in sling-stand frames designed to keep the animal still with a minimum of restraint. Heart rate was monitored every 5 minutes via lead II electrocardiorgram.

The microencapsulated formulations as well as the plain powder of 3,4-bis-(p-toluyloxy)α-[(t-butylamino)methyl]benzenemethanol methanesulfonate in a dose of 240 mcg./kg. (base) were placed in a No. 4 hard gelatin capsule and administered to the animal orally followed by 10 ml. of water. Each of the six dogs was medicated at weekly intervals with either the microencapsulated formulations or the plain powder until each dog had received each produce twice. Two dogs were tested on each experimental day.

For the evaluation of heart rate effects, baseline pulse rates were analyzed to determine the limits within which control values would be expected to lie. Contrasting baseline values for the different experimental periods, days, dogs and observation times (20-, 10- and 0-min. pretreatment) produced 95% confidence limits ranging from 83 to 117% of the mean. Consequently, on any one experimental day, the onset of a drug effect was defined as that first point in time where four successive 5-minute readings were equal to or greater than 1.17 times the mean of a test animal's pretreatment readings. The end of a drug effect was defined as that first point where either four successive 5-minute readings were less than the mean baseline, or in a few instances where the 300-minute time period was reached. The statistic employed in the analysis was the sum of the pulse changes from baseline over the drug effect portion of the time-response curve. The single dog not showing a drug effect was assigned a result of 0 for the sum of the pulse changes.

Since all six dogs received in different order, all possible treatments twice, in six experimental periods, the order effect was assumed to be small relative to other sources of variation.

The microencapsulated formulations of Examples 3B and 3C having dissolution half-lives of 65 and 101 minutes, respectively, were subjected to the above-described test procedures together with 3,4-bis-(p-toluyloxy)-α-[(tert-butylamino)methyl]benzenemethanol methanesulfonate as a plain powder (Reference Compound). The results are given in Tables A and B below.

Table A

Percent Bronchodilation After Intraduodenal Administration of 240 mcg./kg. (base) to Anesthetized Dogs

| Cpd. of Ex. No. | No. of dogs | Time Post-Medication (min.) | | | | | | | |
|---|---|---|---|---|---|---|---|---|---|
| | | 10 | 30 | 60 | 120 | 180 | 240 | 300 | 360 |
| Ref. Cpd. | 7 | 43 ± 8 | 53 ± 8 | 60 ± 9 | 57 ± 6 | 46 ± 6 | 43 ± 7 | 41 ± 6 | 39 ± 7 |
| 3B | 7 | 40 ± 7 | 42 ± 6 | 56 ± 3 | 60 ± 4 | 58 ± 4 | 55 ± 5 | 55 ± 6 | 51 ± 3 |
| 3C | 7 | 26 ± 5 | 27 ± 7 | 36 ± 5 | 46 ± 3 | 42 ± 4 | 33 ± 4 | 36 ± 4 | 35 ± 4 |

Table B

Heart Rate Effect in Unanesthetized Dogs After Oral Administration of 240 mcg/kg (base)

Sum of the Pulse Changes From Baseline ($t_o$) Over the Drug Effect Portion of the Time-Response Curve (beats/min)

| Dog | Ref. Cpd. | Cpd. of Ex. 3B | Cpd. of Ex. 3C |
|---|---|---|---|
| 1 | 1377 | 1948 | 1300 |
| 2 | 1070 | 826 | 459 |
| 3 | 2423 | 369 | 461 |
| 4 | 180 | 1255 | 0 |
| 5 | 2940 | 2053 | 2127 |
| 6 | 404 | 266 | 208 |
| Arithmetic Mean | 1400 | 1120 | 760 |

I claim:

1. A controlled-release pharmaceutical dosage component for hard gelatin capsule unit dosage forms comprising a microcapsule prepared by organic phase separation with polyethylene as a phase separation inducing agent consisting of a film of hydrophobic ethylcellulose polymeric material encapsulating a core substantially in the form of an extruded spherule of approximately 420 to 1190 micron diameter and comprising from about 3 to 80 percent by weight of a bronchodilator agent of the β-adrenergic agonist type (in admixture with a pharmaceutically acceptable excipient), at least 10 percent by weight of microcrystalline cellulose and any remainder being conventional pharmaceutical excipients.

2. A controlled-release pharmaceutical dosage component according to claim 1 wherein the broncholidator agent of the β-adrenergic agonist type is selected from the group consisting of 3,4-dihydroxy-α-[(methylamino)methyl]benzenemethanol, α-[1-(methylamino)ethyl]benzenemethanol, α-(1-aminoethyl)-benzenemethanol, α-(1-aminopropyl)-3,4-dihydroxybenzenemethanol, 3,4-dihydroxy-α-[(isopropylamino)-methyl]benzenemethanol, 3,5-dihydroxy-α-[(isopropylamino)methyl]benzenemethanol, 3,4-dihydroxy-α-<{[2-(3,4-methylenedioxyphenyl)-1-methylethyl]-amino}methyl>benzenemethanol; α[(tert-butylamino)-methyl]-3,4-dihydroxybenzenemethanol, α-[(tert-butylamino)methyl]-3,5-dihydroxybenzenemethanol, 3,4-dihydroxy-α-[1-(isopropylamino)propyl]benzenemethanol, 4-hydroxy-3-(hydroxymethyl)-α-[(tert-butylamino)methyl]benzenemethanol, 4, hydroxy-α-[(isopropylamino)methyl]-3-(methanesulfonamido)benzenemethanol, 3,5-dihydroxy-α-<{[2-(4-hydoxyphenyl)-1-methylethyl]amino}methyl>-benzenemethanol, 3,4-dihydroxy-α-(2-piperidinylmethyl)benzenemethanol, 2-chloro-α-[(isopropylamino)methyl]-benzenemethanol, 3-hydroxy-α-[(methylamino)méthyl]benzenemethanol, 4-hydroxy-α-[(isopropylamino)methyl]benzenemethanol, 4-(p-chlorophenyl)-4-hydroxy-2-methylpyrrolidine, 8-hydroxy-6-[1-hydroxy-2-(isopropylamino)ethyl]quinoline, α-[(tert-butylamino)methyl]-4-hydroxy-3-(methylsulfonylmethyl)benzenemethanol, a compound having the formula

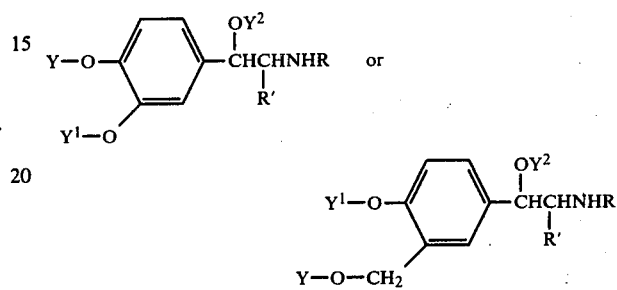

wherein in each of the above formulas:
R is hydrogen, alkyl having 1–4 carbon atoms, or cycloalkyl having 3–6 carbon atoms;
R' is hydrogen or alkyl having 1–3 carbon atoms;
Y is an acyl member which is alkanoyl having 1–22 carbon atoms, alkenoyl having one or two double bonds and having 4–22 carbon atoms, cycloalkyl—$C_nH_{2n}$—CO— having a total of 4–10 carbon atoms of which 3–7 are ring carbon atoms in cycloalkyl and wherein n is zero, one or two, 1- or 2-adamantanecarbonyl, phenoxyacetyl, naphthalenecarbonyl, pyridinecarbonyl, or Z—$C_nH_{2n}$—CO— wherein n is zero, one or two and Z is phenyl or phenyl substituted by 1–3 members of the group consisting of alkyl having 1–4 carbon atoms, alkoxy having 1–4 carbon atoms, halo, trifluoromethyl, dialkylamino having 2–8 carbon atoms, and alkanoylamino having 1–6 carbon atoms; and
$Y^1$ and $Y^2$ are the same or different and are hydrogen or one of the acyl members defined by Y;
and pharmaceutically-acceptable acid-addition salts thereof.

3. A controlled-release pharmaceutical dosage component according to claim 2 wherein the bronchodilator agent is a compound having the formula

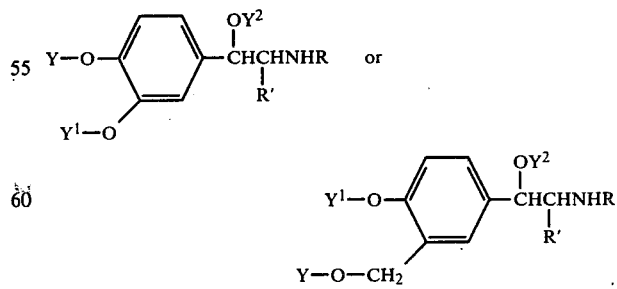

wherein in each of the above formulas:
R is hydrogen, alkyl having 1–4 carbon atoms, or cycloalkyl having 3–6 carbon atoms;
R' is hydrogen or alkyl having 1–3 carbon atoms;

Y is an acyl member which is alkanoyl having 1–22 carbon atoms, alkenoyl having one or two double bonds and having 4–22 carbon atoms, cycloalkyl—$C_nH_{2n}$—CO— having a total of 4–10 carbon atoms of which 3–7 are ring carbon atoms in cycloalkyl and wherein n is zero, one or two, 1- or 2-adamantanecarbonyl, phenoxyacetyl, naphthalenecarbonyl, pyridinecarbonyl, or Z—$C_nH_{2n}$—CO— wherein n is zero, one or two and Z is phenyl or phenyl substituted by 1–3 members of the group consisting of alkyl having 1–4 carbon atoms, alkoxy having 1–4 carbon atoms, halo, trifluoromethyl, dialkylamino having 2–8 carbon atoms, and alkanoylamino having 1–6 carbon atoms; and $Y^1$ and $Y^2$ are the same or different and are hydrogen or one of the acyl members defined by Y;

or a pharmaceutically-acceptable acid-addition salt thereof.

4. A controlled-release pharmaceutical dosage component according to claim 3 wherin the bronchodilator agent is 3,4-bis-(p-toluyloxy)-α-[(tert-butylamino)methyl]benzenemethanol or a pharmaceutically-acceptable acid-addition salt thereof.

5. A controlled-release pharmaceutical dosage component according to claim 4 wherein the film of hydrophobic polymeric material consists of ethylcellulose.

6. A controlled-release pharmaceutical dosage component according to claim 5 wherein the film of ethylcellulose constitutes from about 1 to 5 percent by weight of the microcapsule.

7. A controlled-release pharmaceutical dosage component according to claim 6 wherein the film of ethylcellulose constitutes from about 3 to 4 percent by weight of the microcapsule and the core comprises about 12 percent by weight of 3,4-bis-(p-toluyloxy)-α-[(tert-butylamino)methyl]benzenemethanol or an acid-addition salt thereof, about 19 percent by weight of microcrystalline cellulose, about 50 percent by weight of lactose, about 16 percent by weight of starch and about 3 percent by weight of a starch paste comprising about 15 percent by weight of starch in water.

8. A pharmaceutical formulation in unit dosage form comprising a controlled-release component according to claim 1.

9. A pharmaceutical formulation in unit dosage form comprising a controlled-release component according to claim 3.

10. A pharmaceutical formulation in unit dosage form comprising a controlled-release component according to claim 7.

11. A pharmaceutical formulation according to claim 10 in the form of a hard gelatin capsule.

12. A pharmaceutical formulation according to claim 11 wherein the controlled-release component thereof contains a total of about 4 to 16 mg. of 3,4-bis-(p-toluyloxy)-α-[(tert-butylamino)methyl]benzenemethanol or a pharmaceutically-acceptable acid-addition salt thereof.

* * * * *

UNITED STATES PATENT AND TRADEMARK OFFICE
CERTIFICATE OF CORRECTION

PATENT NO. : 4,153,677
DATED : May 8, 1979
INVENTOR(S) : Philip M. John

It is certified that error appears in the above-identified patent and that said Letters Patent are hereby corrected as shown below:

Column 11, Claim 2, line 66

"8-hydroxy-6-" should read -- 8-hydroxy-5- --.

Signed and Sealed this

Third Day of May 1983

[SEAL]

Attest:

GERALD J. MOSSINGHOFF

Attesting Officer

Commissioner of Patents and Trademarks